(12) United States Patent
Hora

(10) Patent No.: US 11,077,186 B2
(45) Date of Patent: *Aug. 3, 2021

(54) METHODS FOR PREPARING SQUALENE

(71) Applicant: NOVARTIS AG, Basel (CH)

(72) Inventor: Maninder Hora, East Hanover, NJ (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/672,885

(22) Filed: Nov. 4, 2019

(65) Prior Publication Data

US 2020/0061187 A1    Feb. 27, 2020

Related U.S. Application Data

(63) Continuation of application No. 15/842,010, filed on Dec. 14, 2017, now Pat. No. 10,517,947, which is a
(Continued)

(51) Int. Cl.
*A61K 39/39* (2006.01)
*A61K 9/107* (2006.01)
(Continued)

(52) U.S. Cl.
CPC .............. *A61K 39/39* (2013.01); *A61K 9/107* (2013.01); *A61K 39/145* (2013.01); *A61K 47/06* (2013.01);
(Continued)

(58) Field of Classification Search
None
See application file for complete search history.

(56) References Cited

U.S. PATENT DOCUMENTS 6,090,598 A * 7/2000 Yamaguchi ........... C12P 7/6454
426/607
6,165,481 A * 12/2000 Kaiya ...................... A61K 8/31
424/401
(Continued)

FOREIGN PATENT DOCUMENTS

CN         1810744        8/2008
CN       101697204        9/2009
(Continued)

OTHER PUBLICATIONS

Arne Pietsch Philip Jaeger. "Concentration of squalene from shark liver oil by short-path distillation." European Journal of Lipid Science and Technology, vol. 109, 2007, pp. 1077-1082. (Year: 2007).*

(Continued)

*Primary Examiner* — Isaac Shomer
(74) *Attorney, Agent, or Firm* — Duane Morris LLP; Thomas J. Kowalski; Deborah L. Lu

(57) ABSTRACT

An improved method for preparing squalene from a squalene-containing composition, said method comprising the steps of (a) a purification distillation carried out at a temperature $T_1$ (b) a denaturing distillation carried out at a temperature $T_2$; wherein steps (a) and (b) may be performed in either order; $T_1$ and $T_2$ are sufficient to cause squalene to boil; $T_2 > T_1$; and $T_2 > 200°$ C.

18 Claims, 1 Drawing Sheet

Related U.S. Application Data continuation of application No. 15/358,196, filed on Nov. 22, 2016, now Pat. No. 9,867,877, which is a continuation of application No. 14/921,665, filed on Oct. 23, 2015, now Pat. No. 9,545,440, which is a continuation of application No. 13/696,591, filed as application No. PCT/IB2011/001397 on May 12, 2011, now Pat. No. 9,199,897.

(60) Provisional application No. 61/395,448, filed on May 12, 2010.

(51) Int. Cl.
    *A61K 47/06*     (2006.01)
    *C07C 7/04*     (2006.01)
    *A61K 39/145*     (2006.01)
    *B01D 3/10*     (2006.01)
    *C12N 7/00*     (2006.01)
    *B01D 3/14*     (2006.01)
    *B01L 3/10*     (2006.01)
    *A61K 39/00*     (2006.01)

(52) U.S. Cl.
    CPC .............. *B01D 3/10* (2013.01); *B01D 3/143* (2013.01); *B01L 3/10* (2013.01); *C07C 7/04* (2013.01); *C12N 7/00* (2013.01); *A61K 2039/55566* (2013.01); *C12N 2760/16034* (2013.01)

(56) References Cited

U.S. PATENT DOCUMENTS

| | | | |
|---|---|---|---|
| 8,678,184 | B2 | 3/2014 | Kraus et al. |
| 8,778,275 | B2 | 7/2014 | Rueckl et al. |
| 8,871,816 | B2 | 10/2014 | Rueckl et al. |
| 8,895,629 | B2 | 11/2014 | Rueckl et al. |
| 9,199,897 | B2 * | 12/2015 | Hora ........................ C12N 7/00 |
| 9,545,440 | B2 * | 1/2017 | Hora ........................ A61K 39/39 |
| 9,867,877 | B2 * | 1/2018 | Hora ........................ A61K 9/107 |
| 10,517,947 | B2 * | 12/2019 | Hora ........................ A61K 39/39 |
| 2005/0177002 | A1 | 8/2005 | Yamamoto |
| 2005/0250953 | A1 * | 11/2005 | May ....................... C07D 311/72 549/413 |
| 2006/0140969 | A1 | 6/2006 | Valenta et al. |
| 2007/0092525 | A1 | 4/2007 | Vieillard et al. |
| 2009/0047353 | A1 * | 2/2009 | O'Hagan ................ A61P 31/00 424/489 |
| 2013/0129786 | A1 | 5/2013 | Kraus et al. |
| 2015/0017206 | A1 | 1/2015 | Rueckl et al. |
| 2016/0113870 | A1 | 4/2016 | Rueckl et al. |
| 2016/0128937 | A1 | 5/2016 | Rueckl et al. |

FOREIGN PATENT DOCUMENTS

| | | |
|---|---|---|
| CN | 101830770 | 9/2010 |
| JP | 07-309785 | 11/1995 |
| JP | 3484227 | 11/1995 |
| JP | 2000-191550 | 7/2000 |
| JP | 6116171 | 4/2014 |
| WO | 2007/052155 | 5/2007 |
| WO | 08/043774 A1 | 4/2008 |
| WO | 2008/056263 | 5/2008 |
| WO | 2008/142175 | 11/2008 |
| WO | WO-2008142175 A1 * | 11/2008 ............. C07C 7/005 |
| WO | 20101004193 | 1/2010 |
| WO | 2010/023551 | 3/2010 |

OTHER PUBLICATIONS

Google Translate. English translation of WO 2008142175 A1. Downloaded from https://patents.google.com/patent/ WO2008142175A1/en on Sep. 16, 2020, originally published in Spanish on Nov. 27, 2008, pp. 1-8. (Year: 2008).*

Allison, Squalene and Squalane Emulsions as Adjuvants, Methods (1999) 19(1):87-93.

Assignment from inventor Maninder Hora to Novartis Vaccines and Diagnostics, Inc. dated Jan. 5, 2011.

Brito et al., An Alternative Renewable Source of Squalene for use in Emulsion Adjuvants, Vaccine, 29:6282-6288 (2011).

Chua et al., Separation of squalene from palm fatty acid distillate using adsorption chromatography, Eur. J. Lipid Sci. Technol. (2007) vol. 109: 083-1087.

http://www ema.europa.eu/ema/index.jsp?curl=pages/medicines/huma/medicines/00710(humanmed000796.jsp&mid=WCb01ac058001d124, 2 pages, (accessed Sep. 24, 2014).

EMEC, European Medicines Agency, CHMP Assessment Report for FOCETRIA, Pandemic Influenza Vaccines (Surface Antigen, Inactivated, Adjuvanted) A/California/7/2009 (H1N1)v Like Strain (X-179A), Sep. 24, 2009.

Fox et al., Monitoring the effects of component structure and source on formulation stability and adjuvant activity of oil-in-water emulsions, Colloids and Surfaces B: Biointerfaces, 65 (2008) 98-105.

Fox, Squalene Emulsions for Parenteral Vaccine and Drug Delivery, Molecules (2009) 14:3286-3312.

Makidon et al., Characterization of Stability and Nasal Delivery Systems for Immunization with Nanoemulsion-Based Vaccines, Journal of Aerosol Medicine and Pulmonary Drug Delivery, 23(2):77-89 (2010).

Notice of Opposition to a European Patent—Opposition against the grant of European Patent Application No. 2 569 267 BI, Patent Application No. 11738802.5, Mention of date of grant: Dec. 25, 2013, Statement of Opposition filed by GlaxoSmithKline Biologicals, 29 pages, Sep. 25, 2014.

Ott et al., Design and Evaluation of a Safe and Potent Adjuvant for human Vaccines, Vaccine Design, the Subunit and Adjuvant Approach. Pharmaceutical Biotechnology, vol. 6 (1995).

Ott et al., The Adjuvant MF59: A 10-year Perspective, Vaccine Adjuvants: Preparation Methods and Research Protocols, Methods in Molecular Medicine, vol. 42. Chapter 12, p. 211-228 (2000).

Pietsch et al., Concentration of squalene from shark liver oil by short-path distillation, European Journal of Lipid Science and Technology (2007) 109:1077-1082.

Pressure Temperature Nomograph, http://www.sigmaalrich.com/chemistry/solvents/learning-center/nomo-assets.html, accessed Dec. 3, 2015, 1 page.

Response to Notice to Opposition for EP Patent No. 2 569 267, May 2015, 9 pages.

Tham, Distillation—an introduction, Factors Affecting Distillation Column Operation, http://lorien.ncl.ac.uk/ming/distil/distilop.htm, 1997-2005.

Tham, Distillation—an introduction, Vapour Liquid Equilibria, http://lorien.ncl.ac.uk/ming/distil/distilvle.htm, 1997-2005.

Reissue U.S. Appl. No. 14/881,410, filed Oct. 13, 2015.

Reissue U.S. Appl. No. 14/881,575, filed Oct. 13, 2015.

U.S. Appl. No. 15/076,776, filed Mar. 22, 2016.

Vacuum Distillation http://en.wikipedia.org/w/index.pho?title=Vacuumdistillation&oldid=288287808, 3 pages, Apr. 23, 2010.

Dermitec, Topylaude Omega Cream, retrieved from http://dermitec.com/products/cumlaude/skin-care/topylaude/topylaude-omega-cream/, Apr. 20, 2017.

European Medicines Agency. Find medicine—Focetria—Focetria—influenza vaccine (H1N1) (surface antigen, inactivated, adjuvanted), retrieved from: http://www.ema.europa.eu/ema/index.jsp?curl=pages/medicines/human/medicines/00, Sep. 20, 2014.

Farmamica Istituto Ganassini, NeoViderm~Farmamica (NeoViderm 100 ml) retrieved from http://www.farmamica.com/store/neoviderm-100ml.html, Apr. 20. 2017. English Translation attached.

Google. Neoviderm—Google Search, Apr. 20, 2017, retrieved from http://www.google.fr/search? q=neoviderm&biw=1920&bih=839&source=Int&tbs=c.

Huang, Biological and Pharmacological Activities of Squalene and Related Compounds: Potential Uses in Cosmetic Dermatology, Molecules (2009) 14:540-554.

(56) References Cited

OTHER PUBLICATIONS

National Cancer Institute, NCI Drug Dictionary—National Cancer Institute, Apr. 29, 2014, retrieved from: http//www.cancer.gov/drugdictionary?cdrid=717605.
Notice of Opposition against grant of European Patent EP 2 620 423 dated May 30, 2017, issued in European Patent No. 2 620 423.
Assignment from Novartis Vaccines & Diagnostics, Inc. to Novartis AG dated Jan. 14. 2011.
P. Palese, Making Better Influenza Virus Vaccines?, Emerging Infectious Diseases, vol. 12 No. 1 (Jan. 2006) pp. 61-65.
Makidon et al.: Pre-clinical Evaluation of a Novel Nanoemulsion-based Hepatitis B Mucosal Vaccine. PLoS One (2008) vol. 3. Issue 81e2954: 1-15.
ClinicalTrials.gov ID No. NCT01333462: Safety and Immunogenicity Study of Inactivated Nasal Influenza Vaccine NB-1008 (Mar. 2009). Cited in Opposition proceedings for EP Patent No. 3489211 dated Apr. 15, 2021 Retrieved from https://clinicaltrials.gov/ct2/show/study/NCT01333462.
Notice of Opposition filed Apr. 15, 2021, in Opposition proceedings for EP Patent No. 3489211.
Subsequence Statement filed Apr. 15, 2021, in Opposition proceedings for EP Patent No. 3489211.

\* cited by examiner

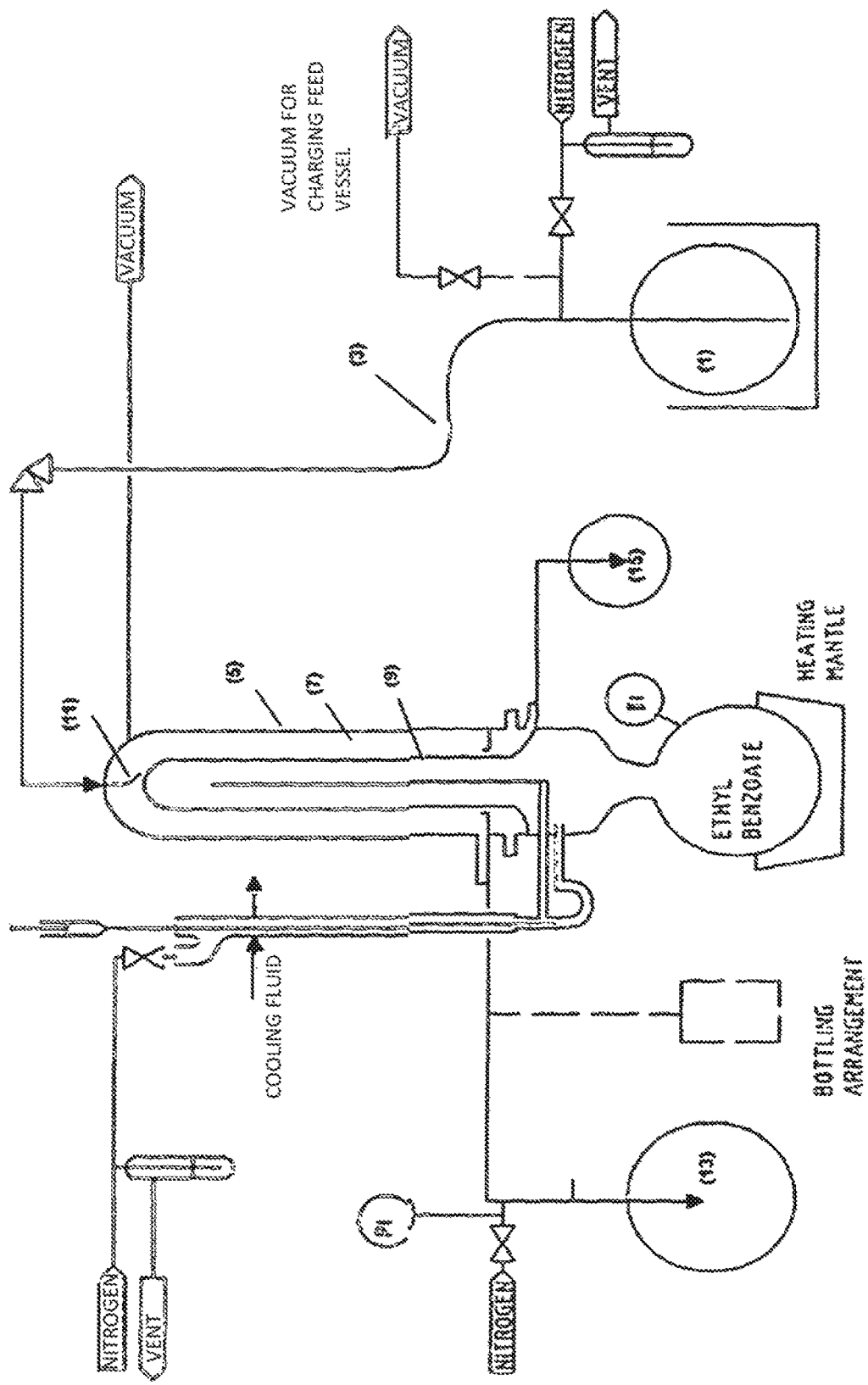

METHODS FOR PREPARING SQUALENE

RELATED APPLICATIONS AND INCORPORATION BY REFERENCE

This application is a continuation of U.S. application Ser. No. 15/842,010 filed Dec. 14, 2017, now allowed, which is a continuation of U.S. application Ser. No. 15/358,196 filed Nov. 22, 2016, which is a continuation of U.S. application Ser. No. 14/921,665 filed Oct. 23, 2015, now U.S. Pat. No. 9,545,440, which is continuation of U.S. application Ser. No. 13/696,591 filed on Feb. 21, 2013, now U.S. Pat. No. 9,199,897, which is a National Phase application of PCT/IB2011/001397 filed May 12, 2011, which claims the benefit of U.S. Provisional Application No. 61/395,448 filed May 12, 2010. The International Application was published as WO 2011/141819 on Nov. 17, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

TECHNICAL FIELD

This invention is in the field of manufacturing squalene having a purity suitable for pharmaceutical applications.

BACKGROUND ART

Shark liver oil contains a branched, unsaturated terpenoid called squalene, ($C_{30}H_{50}$; $[(CH_3)_2C[=CHCH_2CH_2C(CH_3)]_2=CHCH_2-]2$; 2,6,10,15,19,23-hexamethyl-2,6,10,14,18,22-tetracosa-hexaene; CAS RN 7683-64-9). Squalene is known for use in oil-in-water emulsions in human vaccines, for instance the MF59 emulsion that is used for adjuvanting influenza vaccines. Squalene is also used in other pharmaceutical products (e.g. ointments, suppositories) and in cosmetics.

Current sources for squalene are primarily fish oils, and in particular shark liver oils. There can be problems associated with the use of squalene extracted from shark liver oil, particularly if rigorous manufacturing standards (such as those used during the production of MF59 by Novartis) are not upheld. For instance, sharks may be infected by pathogens that are also infectious for humans or that produce substances that are harmful to humans, and TSE or TSE-like shark agents may exist [e.g. references 1-3]. Furthermore, sharks can contain human toxins, such as carchatoxin. In addition, sharks can contain proteins to which humans can be allergic. A common fish protein to which humans are allergic is parvalbumin which is found in sharks. Thus cheap low-grade sources of squalene are not suitable for human pharmaceutical use. The risk of harm to a human recipient may be heightened in situations where squalene is part of an immunological adjuvant because, by definition, the adjuvant may induce a strong unwanted immune response against the impurity.

It would be useful to find further and improved processes for preparing squalene that is suitable for pharmaceutical use, i.e. a product that meets regulatory standards and does not contain contaminants, pathogens, viruses, human toxins or proteins that could be harmful to humans. The process of the present invention is particularly useful for the purification of squalene derived from shark liver oil.

DISCLOSURE OF THE INVENTION

The present invention provides a method for preparing squalene from a composition comprising squalene from an animal source, said method comprising steps of: (a) a purification distillation carried out at a temperature $T_1$; (b) a denaturing distillation carried out at a temperature $T_2$; wherein steps (a) and (b) may be performed in either order; $T_1$ and $T_2$ are sufficient to cause squalene to boil; $T_2 > T_1$; and $T_2 \geq 200°$ C. The animal source is typically a fish source, such as shark liver oil (or an extract thereof) i.e. the invention provides a method for preparing squalene from shark liver oil or from a shark liver oil extract.

The present invention further provides a method for preparing squalene from a squalene-containing composition, comprising steps of (a) a purification distillation carried out at a temperature $T_1$; (b) a denaturing distillation carried out at a temperature $T_2$; wherein steps (a) and (b) may be performed in either order; $T_1$ and $T_2$ are sufficient to cause squalene to boil; $T_1 < 140°$ C. and $T_2 \geq 200°$ C. The squalene-containing composition can usefully be shark liver oil or an extract thereof.

The present invention further provides a method for re-distillation of a composition comprising at least 99% squalene, said re-distillation being a denaturing distillation carried out at a temperature $T_2$, wherein $T_2 \geq 200°$ C. This re-distillation may reduce the moisture content of the composition e.g. to $\leq 0.01\%$.

The method of the present invention can be used to produce a product that is suitable for pharmaceutical applications. In particular, the method of the present invention can be used to produce purified squalene that does not contain contaminants, pathogens, viruses, human toxins or proteins, in particular the protein parvalbumin, which could be harmful to humans.

The present invention further provides a method for the manufacture of an oil-in-water emulsion, comprising preparing an emulsion using squalene prepared according to the methods described above.

The present invention further provides a method for preparing a vaccine composition, comprising preparing an emulsion as described above and combining the emulsion with an antigen.

The present invention further provides a method for preparing a vaccine kit comprising preparing an emulsion as described above and packaging the emulsion into a kit as a kit component together with an antigen component.

The present invention further provides squalene prepared according to the methods of the present invention.

The present invention further provides an oil-in-water emulsion comprising squalene prepared according to the methods of the present invention.

The present invention further provides a vaccine comprising squalene prepared according to the methods of the present invention.

The present invention further provides the use of squalene prepared according to the methods of the present invention in a vaccine.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 shows a schematic of a distillation apparatus which may be used for the purification and/or denaturing distillation steps of the method of the present invention.

PURIFICATION DISTILLATION

The composition comprising squalene may be derived from any suitable source, e.g. black liquor soap skimmings; tall oil soap; crude tall oil; tall oil pitch; sugarcane oil; residues from extraction, degumming, and refining of oils and fats; distillation residues of fatty acids and esters; deodorization distillates of vegetable oils; olive oil; soybean oil; rice bran oil; shark liver oil; beef tallow; coffee oil; fish oil; cod liver oil; wheat germ oil; corn germ oil; palm oils; andiroba oils; and oil from tomato residues. In particular, the composition comprising squalene may be derived from shark liver oil.

The purification distillation removes impurities from a composition comprising squalene to produce a purified composition. The composition comprising squalene is generally a liquid. Prior to purification distillation, the composition comprising squalene may contain impurities such as squalamine; alkylglycerols; fatty acids (e.g. omega-3-fatty acids); vitamins A and D; pristine; triglycerides; glycerol ethers and fatty alcohols.

The purification distillation is carried out at a temperature $T_1$, wherein $T_1$ may be sufficient to cause squalene to boil, i.e. $T_1$ may be greater than or equal to the boiling point of squalene. The boiling point of squalene is 429-430° C. at 760 mm Hg (i.e. 1 atmosphere).

The boiling point of a liquid is the temperature at which the vapor pressure of the liquid phase of a compound equals the external pressure acting on the surface of the liquid. Therefore, the boiling point of squalene, and hence the lower limit of $T_1$, will depend on the external pressure acting on the surface of the composition comprising squalene. This phenomenon is well known in the art and the skilled person would be able to calculate the observed boiling point of squalene at a given distillation pressure used. Alternatively, the skilled person would be able to calculate the required distillation pressure based on a desired observed boiling point of squalene. Such calculations may be carried out using a nomograph.

In one embodiment, the purification distillation can be carried out at a temperature of at least 70° C., e.g. at least 75° C., or at least 80° C. In another embodiment, the purification distillation can be carried out at a temperature of less than 140° C., e.g. less than 130° C., less than 120° C., less than 110° C., less than 100° C. less than 95° C., less than 90° C., or less than 85° C.

In one embodiment, the purification distillation can be carried out in a near vacuum. In particular, the purification distillation can be carried out at a pressure of at least 0.5 μm Hg, e.g. at least 0.75 μm Hg, or at least 1 μm Hg. The purification distillation can be carried out at a pressure of less than 5 μm Hg, e.g. less than 2.5 μm Hg, or less than 2 μm Hg.

Further embodiments of the present invention comprise combinations of the minimum and maximum temperatures and the minimum and maximum pressures recited above.

The purification distillation can result in a composition which comprises at least 95% squalene, e.g. at least 96% squalene, at least 97% squalene, at least 98% squalene, at least 99% squalene, at least 99.5% squalene, at least 99.8% squalene, at least 99.9% squalene, or even 100% squalene.

All percentages quoted herein are percentages by weight and may be measured using gas chromatography (GC). A GC technique may be conducted by injecting a sample of squalene in hexane onto a gas chromatograph equipped with a flame ionization detector (FID). The analysis can be performed on a 30 m×0.32 mm×0.50 mm capillary column maintained at 200° C. for 2 minutes and then ramped at 12° C. per minute to 310° C., where it is held for 9 minutes. The injection port and the FID are maintained at 300° C. and 320° C. respectively. Identity of the squalene peak is established using GC/MS (gas chromatography using a mass selective detector). Purity is reported as the area of the squalene peak as a percentage of the sum of the areas of all the peaks in the chromatogram.

The purification distillation may be carried out prior to the denaturing distillation, resulting in a purified composition. Alternatively, the purification distillation may be carried out after the denaturing distillation, resulting in a denatured, purified composition.

Denaturing Distillation

Sharks, and therefore squalene derived from shark-liver oil, can contain proteins to which humans are allergic. A common fish protein to which humans may be allergic is parvalbumin, which is found in sharks. In addition, contaminant proteins or materials may have been introduced to the squalene composition, e.g. following the purification distillation or as degradation products of the squalene. Possible contaminant proteins or materials include acetone, acetaldehyde, formaldehyde, and water. Advantageously, the denaturing distillation step denatures and/or removes proteins, in particular parvalbumin and any contaminant proteins, from the composition comprising squalene, thus providing a denatured composition. A further advantage of the method of the present invention is that the denaturing distillation can ensure that any potential viruses present in the composition comprising squalene are inactivated and/or removed from the purified composition. The denatured composition is therefore safer for human use than a non-denatured composition.

Without wishing to be bound by theory, the boiling point of squalene will depend on the external pressure acting on the surface of the composition comprising squalene. However, the temperature at which any proteins present in the composition comprising squalene will be denatured is generally independent of the external pressure acting on the surface of the composition comprising squalene. Therefore, the denaturing distillation may be carried out at a specific temperature, irrespective of the pressure under which the distillation is performed. In particular, the denaturing distillation may be carried out at a temperature $T_2$, wherein $T_2$ may be greater than or equal to 200° C. e.g. greater than or equal to 205° C., greater than or equal to 210° C., greater than or equal to 215° C., greater than or equal to 220° C., greater than or equal to 230° C., greater than or equal to 240° C., greater than or equal to 250° C., or greater than or equal to 260° C.

The denaturing distillation may be carried out at a temperature of less than 500° C., e.g. less than 480° C., less than 450° C., less than 420° C., less than 400° C., less than 350° C., or less than 300° C.

The denaturing distillation can be carried out at a near vacuum. In particular, the denaturing distillation can be carried out at a pressure of at least 0.5 mm Hg, e.g. at least 0.6 mm Hg, at least 0.7 mm Hg, or at least 0.8 mm Hg. The denaturing distillation can be carried out at a pressure of less than 5 mm Hg, e.g. less than 4 mm Hg, less than 3 mm Hg, less than 2 mm Hg, less than 1.5 mm Hg, less than 1 mm Hg, or less than 0.9 mm Hg.

Further embodiments of the present invention comprise combinations of the minimum and maximum temperatures and the minimum and maximum pressures recited above.

To carry out the denaturing distillation at such a high temperature, it may be advantageous to use an apparatus in which the composition comprising squalene is brought into contact with a hot surface. The hot surface may be maintained at the temperature $T_2$, as defined above, and the pressure surrounding the hot surface may be the pressures defined above for the denaturing distillation. The pressure surrounding the hot surface may be selected to ensure that the observed boiling point of squalene is $T_2$ or less. As the composition comprising squalene is contacted with the hot surface, those components of the composition, including squalene, whose boiling point is below $T_2$ at the pressure surrounding the hot surface will volatilize. Non-volatile components, e.g. proteins, remain on the hot surface and may be denatured and separated from the squalene.

Prior to the denaturing distillation, the composition comprising squalene may comprise from 85% to 99.9% squalene, e.g. from 90% to 99.5% squalene, from 95% to 99.5% squalene, or from 97% to 99.5% squalene.

The denaturing distillation can produce a squalene composition having a higher percentage of squalene. In particular, the denaturing distillation produces can result in a denatured composition comprising at least 95% squalene, e.g. at least 99% squalene, at least 99.5% squalene, at least 99.9% squalene, or even 100% squalene.

The denaturing distillation can result in a denatured composition comprising less than 0.5% protein, e.g. less than 0.1% protein, less than 0.01% protein, or 0% protein. Therefore, the present invention provides squalene comprising less than 0.5% protein, e.g. less than 0.1% protein, less than 0.01% protein, or 0% protein.

In one embodiment, the denaturing distillation may be carried out after the purification distillation, resulting in a purified, denatured composition.

$T_2$ may be greater than $T_1$. In particular, $T_2$-$T_1$ may be from 10° C. to 300° C., e.g. from 30° C. to 250° C., from 50° C. to 200° C., or from 80° C. to 150° C.

Solvents

To avoid the introduction of impurities to the composition comprising squalene, which is particularly important if the squalene composition is intended for use in vaccines, the purification and denaturing distillations may be carried out without the addition of solvents.

Saponification

The composition comprising squalene may be subjected to saponification. Saponification will usually be carried out prior to distillation steps (a) and (b), discussed above. Alternatively, saponification may be carried out in between distillation steps (a) and (b), in whichever order they are performed. Alternatively, but unusually, saponification may be carried out after distillation steps (a) and (b). Saponification may destroy proteins present in the composition comprising squalene. However, saponification may not remove all the proteins present. Any residual proteins remaining in the composition comprising squalene after saponification may be removed though a denaturing distillation step. The combination of saponification and denaturing distillation is advantageous as it improves the chances that the squalene does not contain any proteins.

Saponification is the hydrolysis of an ester under basic conditions to form an alcohol and the salt of a carboxylic acid. During saponification of the composition comprising squalene, a base (e.g. NaOH or KOH) is added to the composition which can cause the fatty acid esters (e.g. the triglycerides) to convert into soap. Saponification may be advantageous because it can increase the difference between the boiling points of the saponified products and the boiling points of the unsaponified products, making separation by distillation, e.g. the purification and/or the denaturing distillation, more efficient. Alternatively, the saponified products may be removed by another means, e.g. by centrifugation.

The removal of the fatty acid esters by saponification can result in a saponified composition comprising squalene, which can be of improved purity (i.e. a higher % of squalene) compared to the unsaponified composition comprising squalene.

Squalene Characterization

The squalene produced by the method of the present invention may have a saponification value of less than 4 mg/ml, e.g. less than 3 mg/ml, less than 2 mg/ml, or less than 1 mg/ml. This measurement indicates the amount of saponifiable species present in the squalene. The saponification value may be determined as the hydrolyzing and neutralizing equivalents of sodium hydroxide as described in US Pharmacopeia (USP) <401>. A saponification value obtained using NaOH can be converted to a KOH values by multiplying it by the ratio of the molecular weights of KOH and NaOH (1.403).

The squalene produced by the method of the present invention may have an acid value of less than or equal to 1 mg KOH/g, e.g. less than or equal to 0.8 mg KOH/g, less than or equal to 0.6 mg KOH/g, less than or equal to 0.5 mg KOH/g, less than or equal to 0.4 mg KOH/g, less than or equal to 0.2 mg KOH/g, less than or equal to 0.1 mg KOH/g, less than or equal to 0.05 mg KOH/g, less than or equal to 0.03 mg KOH/g, less than or equal to 0.02 mg KOH/g, or less than or equal to 0.01 mg KOH/g. The acid value may be determined as the as the neutralizing equivalents of potassium hydroxide consumed by squalene as described in USP <401>.

Oil-in-Water Emulsions

Once the composition comprising squalene has been prepared as described above, it can be used for preparation of downstream products e.g. medicines, oil-in-water emulsion adjuvants, etc.

To avoid contamination, it is preferable that squalene be kept sterile following distillation treatment and prior to the preparation of the downstream product. For example, if the downstream product is an emulsion, the distillation and emulsion apparatuses could form a closed system to avoid contamination of the squalene prior to formation of the emulsion. Alternatively or in addition, the squalene could be kept under an inert atmosphere, e.g. nitrogen, prior to preparation of the downstream product.

Oil-in-water emulsions have been found to be particularly suitable for use in adjuvanting vaccines. Emulsions prepared according to the invention include squalene and at least one surfactant, in addition to an aqueous component. The emulsions may contain additional oils. Ideally, the oil(s) and surfactant(s) are biodegradable (metabolisable) and biocompatible.

Oil combinations of squalene and tocopherols can be used. Where a composition includes a tocopherol, any of the α β γ δ ε or ξ tocopherols can be used, but α-tocopherols are preferred. D-α-tocopherol and DL-α-tocopherol can both be used. A preferred α-tocopherol is DL-α-tocopherol. The tocopherol can take several forms e.g. different salts and/or isomers. Salts include organic salts, such as succinate, acetate, nicotinate, etc. If a salt of a tocopherol is used, the preferred salt is the succinate. An oil combination comprising squalene and a tocopherol (e.g. DL-α-tocopherol) is useful.

An oil content in the range of 2-20% (by volume) is typical.

The aqueous component can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. Buffers will typically be included in the 5-20 mM range.

The surfactant is preferably biodegradable (metabolisable) and biocompatible. Surfactants can be classified by their 'HLB' (hydrophile/lipophile balance), where a HLB in the range 1-10 generally means that the surfactant is more soluble in oil than in water, and a HLB in the range 10-20 are more soluble in water than in oil. Emulsions preferably comprise at least one surfactant that has a HLB of at least 10 e.g. at least 15, or preferably at least 16.

The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the SPANs), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. Tween 80, with a HLB of 15.0) and a surfactant with a HLB value in the range of 1-10 (e.g. Span 85, with a HLB of 1.8).

Preferred amounts of surfactants (% by weight) are: polyoxyethylene sorbitan esters (such as Tween 80) 0.01 to 2%; octyl- or nonylphenoxy polyoxyethanols (such as Triton X-100, or other Triton series detergents) 0.001 to 0.1%; polyoxyethylene ethers (such as laureth 9) 0.1 to 20%.

Squalene-containing oil-in-water emulsions containing polysorbate 80 surfactant are preferred.

The oil-in-water emulsion may be manufactured using a method comprising the steps of: (i) preparation of a first emulsion having a first average oil droplet size, also known as a preliminary emulsion or a pre-emulsion; (ii) microfluidization of the first emulsion to form a second emulsion having a second average oil droplet size which is less than the first average oil droplet size; and (iii) filtration of the second emulsion. The first emulsion may be prepared through homogenization.

The oil droplets in the emulsion are generally less than 5.mu·m in diameter, and may even have a sub-micron diameter, with these small sizes conveniently being achieved with a microfluidiser to provide stable emulsions. Droplets with a size less than 220 nm are preferred as they can be subjected to filter sterilization.

Specific oil-in-water emulsion adjuvants that can be made using squalene prepared according to the invention include, but are not limited to:

An emulsion of squalene, polysorbate 80 (Tween 80), and sorbitan trioleate (Span 85). The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [4-6], as described in more detail in Chapter 10 of ref. 7 and chapter 12 of ref. 8. The MF59 emulsion advantageously includes citrate ions e.g. 10 mM sodium citrate buffer.

An emulsion of squalene, a tocopherol (ideally DL-.alpha.-tocopherol), and polysorbate 80. These emulsions may have (by weight) from 2 to 10% squalene, from 2 to 10% tocopherol and from 0.3 to 3% polysorbate 80, e.g. 4.3% squalene, 4.7% tocopherol and 1.9% polysorbate 80. The weight ratio of squalene:tocopherol is preferably <1 (e.g. 0.90) as this can provide a more stable emulsion. Squalene and polysorbate 80 may be present at a volume ratio of about 5:2 or at a weight ratio of about 11:5. One such emulsion can be made by dissolving polysorbate 80 in PBS to give a 2% solution, then mixing 90 ml of this solution with a mixture of (5 g of DL-.alpha.-tocopherol and 5 ml squalene), then microfluidising the mixture. The resulting emulsion has submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [9].

An emulsion of squalene, a tocopherol, and a Triton detergent (e.g. Triton X-100). The emulsion may also include a 3d-MPL. The emulsion may contain a phosphate buffer.

An emulsion comprising squalene, a polysorbate (e.g. polysorbate 80), a Triton detergent (e.g. Triton X-100) and a tocopherol (e.g. an .alpha.-tocopherol succinate). The emulsion may include these three components at a mass ratio of about 75:11:10 (e.g. 7504 ml polysorbate 80, 110 μg/ml Triton X-100 and 100 μg/ml .alpha.-tocopherol succinate), and these concentrations should include any contribution of these components from antigens. The emulsion may also include a 3d-MPL.

The emulsion may also include a saponin, such as QS21. The aqueous phase may contain a phosphate buffer.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [10]. The emulsion may also include one or more of: alditol; a cryoprotective agent (e.g. a sugar, such as dodecylmaltoside and/or sucrose); and/or an alkylpolyglycoside. The emulsion may include a TLR4 agonist [11]. Such emulsions may be lyophilized.

An emulsion of squalene, poloxamer 105 and Abil-Care [12]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

The compositions of these emulsions, expressed above in percentage terms, may be modified by dilution or concentration (e.g. by an integer, such as 2 or 3 or by a fraction, such as ⅔ or ¾), in which their ratios stay the same. For instance, a 2-fold concentrated MF59 would have about 10% squalene, about 1% polysorbate 80 and about 1% sorbitan trioleate. Concentrated forms can be diluted (e.g. with an antigen solution) to give a desired final concentration of emulsion.

Emulsions of the invention are ideally stored at between 2° C. and 8° C. They should not be frozen. They should ideally be kept out of direct light. In particular, squalene-containing emulsions and vaccines of the invention should be protected to avoid photochemical breakdown of squalene. If emulsions of the invention are stored then this is preferably in an inert atmosphere e.g. $N_2$ or argon.

Vaccines

Although it is possible to administer oil-in-water emulsion adjuvants on their own to patients (e.g. to provide an adjuvant effect for an antigen that has been separately administered to the patient), it is more usual to admix the adjuvant with an antigen prior to administration, to form an immunogenic composition e.g. a vaccine. Mixing of emulsion and antigen may take place extemporaneously, at the time of use, or can take place during vaccine manufacture, prior to filling. The methods of the invention can be applied in both situations.

Thus a method of the invention may include a further process step of admixing an emulsion comprising squalene prepared according to the present invention with an antigen component. As an alternative, it may include a further step of packaging the adjuvant into a kit as a kit component together with an antigen component.

Overall, therefore, the invention can be used when preparing mixed vaccines or when preparing kits including antigen and adjuvant ready for mixing. Where mixing takes place during manufacture then the volumes of bulk antigen and emulsion that are mixed will typically be greater than 1 liter e.g. ≥5 liters, ≥10 liters, ≥20 liters, ≥50 liters, etc. Where mixing takes place at the point of use then the volumes that are mixed will typically be smaller than 1 milliliter e.g. ≤0.6 ml, ≤0.5 ml, ≤0.4 ml, ≤0.3 ml, ≤0.2 ml, etc. In both cases it is usual for substantially equal volumes of emulsion and antigen solution to be mixed i.e. substantially 1:1 (e.g. between 1.1:1 and 1:1.1, preferably between 1.05:1 and 1:1.05, and more preferably between 1.025:1 and 1:1.025). In some embodiments, however, an excess of emulsion or an excess of antigen may be used [13]. Where an excess volume of one component is used, the excess will generally be at least 1.5:1 e.g. ≥2:1, ≥2.5:1, ≥3:1, ≥4:1, ≥5:1, etc.

Where antigen and adjuvant are presented as separate components within a kit, they are physically separate from each other within the kit, and this separation can be achieved in various ways. For instance, the components may be in separate containers, such as vials. The contents of two vials can then be mixed when needed e.g. by removing the contents of one vial and adding them to the other vial, or by separately removing the contents of both vials and mixing them in a third container.

In another arrangement, one of the kit components is in a syringe and the other is in a container such as a vial. The syringe can be used (e.g. with a needle) to insert its contents into the vial for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe e.g. a dual-chamber syringe, such as those disclosed in references 14-21 etc. When the syringe is actuated (e.g. during administration to a patient) then the contents of the two chambers are mixed. This arrangement avoids the need for a separate mixing step at time of use.

The contents of the various kit components will generally all be in liquid form. In some arrangements, a component (typically the antigen component rather than the emulsion component) is in dry form (e.g. in a lyophilized form), with the other component being in liquid form. The two components can be mixed in order to reactivate the dry component and give a liquid composition for administration to a patient. A lyophilized component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses a liquid emulsion component in a pre-filled syringe and a lyophilized antigen component in a vial.

If vaccines contain components in addition to emulsion and antigen then these further components may be included in one these two kit components, or may be part of a third kit component.

Suitable containers for mixed vaccines of the invention, or for individual kit components, include vials and disposable syringes. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. In one embodiment, a vial has a butyl rubber stopper. The vial may include a single dose of vaccine/component, or it may include more than one dose (a 'multidose' vial) e.g. 10 doses. In one embodiment, a vial includes 10×0.25 ml doses of emulsion. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilized material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where a composition/component is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield.

The emulsion may be diluted with a buffer prior to packaging into a vial or a syringe. Typical buffers include: a phosphate buffer; a Tris buffer; a borate buffer; a succinate buffer; a histidine buffer; or a citrate buffer. Dilution can reduce the concentration of the adjuvant's components while retaining their relative proportions e.g. to provide a "half-strength" adjuvant.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

Various antigens can be used with oil-in-water emulsions, including but not limited to: viral antigens, such as viral surface proteins; bacterial antigens, such as protein and/or saccharide antigens; fungal antigens; parasite antigens; and tumor antigens. The invention is particularly useful for vaccines against influenza virus, HIV, hookworm, hepatitis B virus, herpes simplex virus, rabies, respiratory syncytial virus, cytomegalovirus, *Staphylococcus aureus, chlamydia*, SARS coronavirus, varicella zoster virus, *Streptococcus pneumoniae, Neisseria meningitidis, Mycobacterium tuberculosis, Bacillus anthracis*, Epstein Barr virus, human papillomavirus, etc. For example:

Influenza virus antigens. These may take the form of a live virus or an inactivated virus. Where an inactivated virus is used, the vaccine may comprise whole virion, split virion, or purified surface antigens (including hemagglutinin and, usually, also including neuraminidase). Influenza antigens can also be presented in the form of virosomes. The antigens may have any hemagglutinin subtype, selected from H1, H2, H3, H4, H5, H6, H7, H8, H9, H10, H11, H12, H13, H14, H15 and/or H16. Vaccine may include antigen(s) from one or more (e.g. 1, 2, 3, 4 or more) influenza virus strains, including influenza A virus and/or influenza B virus, e.g. a monovalent A/H5N1 or A/H1N1 vaccine, or a trivalent A/H1N1+A/H3N2+B vaccine. The influenza virus may be a reassortant strain, and may have been obtained by reverse genetics techniques [e.g. 22-26]. Thus the virus may include one or more RNA segments from a A/PR/ 8/34 virus (typically 6 segments from A/PR/8/34, with the HA and N segments being from a vaccine strain, i.e. a 6:2 reassortant). The viruses used as the source of the antigens can be grown either on eggs (e.g. embryonated hen eggs) or on cell culture. Where cell culture is used, the cell substrate will typically be a mammalian cell line, such as MDCK; CHO; 293T; BHK; Vero; MRC-5; PER.C6; WI-38; etc. Preferred mammalian cell lines for growing influenza viruses include: MDCK cells [27-30], derived from Madin Darby canine kidney; Vero cells [31-33], derived from African green monkey kidney; or PER.C6 cells [34], derived from human embryonic retinoblasts. Where virus has been grown on a mammalian cell line then the composition will advantageously be free from egg proteins (e.g. ovalbumin and ovomucoid) and from chicken DNA, thereby reducing allergenicity. Unit doses of vaccine are typically standardized by reference to hemagglutinin (HA) content, typically measured by SRID. Existing vaccines typically contain about 15 µg of HA per strain, although lower doses can be used, particularly when using an adjuvant. Fractional doses such as ½ (i.e. 7.5 µg HA per strain), ¼ and ⅛ have been used [35,36], as have higher doses (e.g. 3× or 9× doses [37,38]). Thus vaccines may include between 0.1 and 150 µg of HA per influenza strain, preferably between 0.1 and 50 µg e.g. 0.1-20 µg, 0.1-15 µg, 0.1-10 µg, 0.5-5 µg, etc. Particular doses include e.g. about 15, about 10, about 7.5, about 5, about 3.8, about 3.75, about 1.9, about 1.5, etc. per strain. Human immunodeficiency virus, including HIV-1 and HIV-2. The antigen will typically be an envelope antigen.

Hepatitis B virus surface antigens. This antigen is preferably obtained by recombinant DNA methods e.g. after expression in a *Saccharomyces cerevisiae* yeast. Unlike native viral HBsAg, the recombinant yeast-expressed antigen is non-glycosylated. It can be in the form of substantially-spherical particles (average diameter of about 20 nm), including a lipid matrix comprising phospholipids. Unlike native HBsAg particles, the yeast-expressed particles may include phosphatidylinositol. The HBsAg may be from any of subtypes ayw1, ayw2, ayw3, ayw4, ayr, adw2, adw4, adrq− and adrq+.

Hookworm, particularly as seen in canines (*Ancylostoma caninum*). This antigen may be recombinant Ac-MTP-1 (astacin-like metalloprotease) and/or an aspartic hemoglobinase (Ac-APR-1), which may be expressed in a baculovirus/insect cell system as a secreted protein [39,40].

Herpes simplex virus antigens (HSV). A preferred HSV antigen for use with the invention is membrane glycoprotein gD. It is preferred to use gD from a HSV-2 strain ('gD2' antigen). The composition can use a form of gD in which the C-terminal membrane anchor region has been deleted [41] e.g. a truncated gD comprising amino acids 1-306 of the natural protein with the addition of asparagine and glutamine at the C-terminus. This form of the protein includes the signal peptide which is cleaved to yield a mature 283 amino acid protein. Deletion of the anchor allows the protein to be prepared in soluble form.

Human papillomavirus antigens (HPV). Preferred HPV antigens for use with the invention are L1 capsid proteins, which can assemble to form structures known as virus-like particles (VLPs). The VLPs can be produced by recombinant expression of L1 in yeast cells (e.g. in *S. cerevisiae*) or in insect cells (e.g. in *Spodoptera* cells, such as *S. frugiperda*, or in *Drosophila* cells).

For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [42]. In addition to HPV-16 and HPV-18 strains, it is also possible to include L1 VLPs from HPV-6 and HPV-11 strains. The use of oncogenic HPV strains is also possible. A vaccine may include between 20-60 μg/ml (e.g. about 40 μg/ml) of L1 per HPV strain.

Anthrax antigens. Anthrax is caused by *Bacillus anthracis*. Suitable *B. anthracis* antigens include A-components (lethal factor (LF) and edema factor (EF)), both of which can share a common B-component known as protective antigen (PA). The antigens may optionally be detoxified. Further details can be found in references [43 to 45].

*S. aureus* antigens. A variety of *S. aureus* antigens are known. Suitable antigens include capsular saccharides (e.g. from a type 5 and/or type 8 strain) and proteins (e.g. IsdB, Hla, etc.). Capsular saccharide antigens are ideally conjugated to a carrier protein.

*S. pneumoniae* antigens. A variety of *S. pneumoniae* antigens are known. Suitable antigens include capsular saccharides (e.g. from one or more of serotypes 1, 4, 5, 6B, 7F, 9V, 14, 18C, 19F, and/or 23F) and proteins (e.g. pneumolysin, detoxified pneumolysin, polyhistidine triad protein D (PhtD), etc.). Capsular saccharide antigens are ideally conjugated to a carrier protein.

Cancer antigens. A variety of tumour-specific antigens are known. The invention may be used with antigens that elicit an immunotherapeutic response against lung cancer, A solution of the antigen will normally be mixed with the squalene-containing emulsion e.g. at a 1:1 volume ratio. This mixing can either be performed by a vaccine manufacturer, prior to filling, or can be performed at the point of use, by a healthcare worker.

Pharmaceutical Compositions

Compositions made using the methods of the invention are pharmaceutically acceptable. They may include components in addition to the squalene-containing emulsion and the optional antigen.

The composition may include a preservative such as thiomersal or 2-phenoxyethanol. It is preferred, however, that the vaccine should be substantially free from (i.e. less than 5 μg/ml) mercurial material e.g. thiomersal-free [46, 47]. Vaccines and components containing no mercury are more preferred.

The pH of a composition will generally be between 5.0 and 8.1, and more typically between 6.0 and 8.0 e.g. between 6.5 and 7.5. A process of the invention may therefore include a step of adjusting the pH of the vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunization, or may include material for multiple immunizations (i.e. a 'multidose' kit). The inclusion of a preservative is preferred in multidose arrangements.

Vaccines are typically administered in a dosage volume of about 0.5 ml, although a half dose (i.e. about 0.25 ml) may be administered to children.

Methods of Treatment, and Administration of the Vaccine

The invention provides kits and compositions prepared using the methods of the invention. The compositions prepared according to the methods of the invention are suitable for administration to human patients, and the invention provides a method of raising an immune response in a patient, comprising the step of administering such a composition to the patient.

The invention also provides these kits and compositions for use as medicaments.

The invention also provides the use of: (i) an aqueous preparation of an antigen; and (ii) an oil-in-water emulsion comprising squalene prepared according to the invention, in the manufacture of a medicament for raising an immune response in a patient.

The immune response raised by these methods and uses will generally include an antibody response, preferably a protective antibody response.

The compositions can be administered in various ways. The most preferred immunization route is by intramuscular injection (e.g. into the arm or leg), but other available routes include subcutaneous injection, intranasal [48-50], oral [51], intradermal [52,53], transcutaneous, transdermal [54], etc.

Vaccines prepared according to the invention may be used to treat both children and adults. The patient may be less than 1 year old, 1-5 years old, 5-15 years old, 15-55 years old, or at least 55 years old. The patient may be elderly (e.g. ≤50 years old, preferably ≥65 years), the young (e.g. ≤5 years old), hospitalized patients, healthcare workers, armed service and military personnel, pregnant women, the chronically ill, immunodeficient patients, and people travelling abroad. The vaccines are not suitable solely for these groups, however, and may be used more generally in a population.

Vaccines of the invention may be administered to patients at substantially the same time as (e.g. during the same medical consultation or visit to a healthcare professional) other vaccines.

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

Unless specifically stated, a process comprising a step of mixing two or more components does not require any specific order of mixing. Thus components can be mixed in any order. Where there are three components then two components can be combined with each other, and then the combination may be combined with the third component, etc.

The various steps of the methods may be carried out at the same or different times, in the same or different geographical locations, e.g. countries, and by the same or different people or entities.

MODES FOR CARRYING OUT THE INVENTION

Example 1

FIG. 1 shows a schematic of a distillation apparatus which may be used for the purification and/or denaturing distillation steps of the method of the present invention. The process described with reference to FIG. 1 may be carried out without the addition of any solvent to the composition comprising squalene. In the embodiment shown in FIG. 1, the composition comprising squalene is placed in a feed vessel (1) overlaid with nitrogen. One end of an inlet line (3) has a polypropylene prefilter and is placed in the feed vessel, while the other end of the inlet line has a stainless steel needle (19-ga.) which is inserted into the top of a distillation apparatus (5). The distillation apparatus comprises a chamber (7) shaped like a tube with a cylindrical "hot finger" (9) protruding through the centre. Ethyl benzoate, which has a boiling point of 212° C., is heated below the finger to provide heat to the wall of the hot finger. Although ethyl benzoate is used in this embodiment, it is clear that a solvent having a higher boiling point could be used to increase the temperature of the hot finger. During distillation, the distillation apparatus may be evacuated. The composition comprising squalene may be drawn into the distillation apparatus, e.g. through the use of a lower pressure within the distillation apparatus, through the stainless steel needle and dripped (11) onto the heated wall of the hot finger. As the composition comprising squalene is heated, those components whose boiling point is below 212° C. at the pressure within the distillation apparatus will volatilize. In order to volatilize squalene using the system of FIG. 1, the pressure within the distillation apparatus should be selected to lower the boiling point of squalene to 212° C. or less (e.g. approximately 1.5 mm Hg or less). The volatilized components will condense on the outer wall of the chamber (7), which will be cooled by the ambient air, and will run down the walls into a collection flask (13), which may also be under vacuum. Non-volatile components, e.g. proteins, remain on the wall of the hot finger and flow down into the residue flask (15). Extremely volatile components may be drawn off through the vacuum line, reducing their levels in the squalene condensate.

Squalene which has already been subjected to purification distillation was distilled using this apparatus. Regardless of source, the final squalene regularly had a purity of ≥99.9%, an acid value of <0.03 mg KOH/g, and a saponification value <2 mg/g. The denaturing distillation reduced the moisture content of the squalene e.g. from 0.022% to 0.010%, from 0.006 to 0.005%, or from 0.010% to 0.006%.

Example 2—Measurement of the Saponification Value

The saponification value is the number of mg of potassium hydroxide required to neutralize the free acids and saponify the esters contained in 1.0 g of the substance.

Procedure (USP <401>): place 1.5 g to 2 g of the substance in a tared, 250 mL flask, weigh accurately, and add it to 25.0 mL of a 0.5 N alcoholic potassium hydroxide. Heat the flask on a steam bath, under a suitable condenser to maintain reflux for 30 minutes, frequently rotating the contents. Then add 1 mL of phenolphthalein TS, and titrate the excess potassium hydroxide with 0.5N hydrochloric acid VS. Perform a blank determination under the same conditions. The difference between the volumes, in mL, of 0.5 N hydrochloric acid consumed in the actual test and in the blank test, multiplied by 56.1 and the exact normality of the 0.5N hydrochloric acid VS, and divided by the weight in g of the specimen taken, is the saponification value.

Depending on the source of the squalene, a saponification value of <1.4 mg/g could be obtained.

Example 3—Measurement of the Acid Value

The acidity of fats and fixed oils may be expressed as the number of mL of 0.1 N alkali required to neutralize the free acids in 10.0 g of substance. The Acid Value is the number of mg of alkali required to neutralize the free acids in 1.0 g of the substance.

Procedure (USP <401>): dissolve about 10.0 g of the substance, accurately weighed, in 50 mL of a mixture of equal volumes of alcohol and ether (which has been neutralized to phenolphthalein with 0.1 N sodium hydroxide) contained in a flask. If the test specimen does not dissolve in the cold solvent, connect the flask with a suitable condenser and warm slowly, with frequent shaking, until the specimen dissolves. Add 1 mL of phenolphthalein TS, and titrate with 0.1 N sodium hydroxide VS until the solution remains faintly pink after shaking for 30 seconds. Calculate either the Acid Value. If the volume of 0.1 N alkali VS required for the titration is less than 2 mL, a more dilute titrant may be used, or the sample size may be adjusted accordingly. The results may be expressed in terms of the volume of titrant or in terms of the equivalent volume of 0.1 N sodium hydroxide.

Depending on the source of the squalene, an acid value of 0.03 mg KOH/g could be obtained.

Example 4—Spiking Studies

A number of spiking studies were carried out to demonstrate the efficacy of the denaturing distillation.

To determine the levels of impurity removed by the denaturing distillation, a squalene composition was spiked with specified quantities of contaminants (e.g. water) as well as possible decomposition products of the squalene (e.g. formaldehyde, acetaldehyde and acetone). The spiked solutions underwent a denaturing distillation according to the present invention and were analyzed for the spiked species.

4 kg of a squalene composition was spiked e.g. with 0.3 mL (0.2 g) of acetaldehyde (>99.5% purity), 0.3 mL (0.2 g) of acetone (>99.9% purity), 0.55 mL of 37 wt. % aqueous solution of formaldehyde (0.2 g) and 3.65 g water prior to a denaturing distillation as described in example 1. The distillate was collected in three fractions and analyzed for the spiked species alongside the spiked starting material. The results are presented in Table 1 below:

TABLE 1

| Test/Method | Spiked Starting Material | Denaturing distillation fractions | | | Waste Non-volatile Residue |
|---|---|---|---|---|---|
| | | First Fraction | Second Fraction | Third Fraction | |
| Moisture Content (%) | 0.02 | 0.03 | 0.02 | 0.02 | N/A |
| Acetone (mg/Kg or ppm) | 50.9 | 5.0 | 5.7 | 1.1 | N/A |
| Acetaldehyde (mg/Kg or ppm) | 12.4 | 0.9 | 1.9 | 0.9 | N/A |
| Formaldehyde (mg/Kg or ppm) | 2.2 | 0.7 | 0.9 | not detected | N/A |

The results in Table 1 show that the acetone, acetaldehyde and formaldehyde concentrations all decreased following the denaturing distillation.

It will be understood that the invention has been described by way of example only and modifications may be made whilst remaining within the scope and spirit of the invention.

The invention claimed is:

1. A method for preparing squalene from a composition comprising squalene from an animal source, said method comprising steps of (a) a purification distillation carried out at a temperature $T_1$, (b) a denaturing distillation carried out at a temperature $T_2$ and at a pressure of from 0.5 mm Hg to 5.0 mm Hg; wherein steps (a) and (b) may be performed in either order; $T_1$ and $T_2$ are sufficient to cause squalene to boil; $T_2 > T_1$; and $T_2 \geq 200°$ C.

2. The method of claim 1, wherein the composition of squalene from an animal source prior to distillation comprises one or more proteins.

3. The method of claim 2, wherein the composition of squalene from an animal source prior to distillation comprises parvalbumin.

4. The method of claim 1, wherein the purification distillation is carried out at a temperature of from 70 to 100° C.

5. The method of claim 1, wherein the purification distillation is carried out at a pressure of from 0.5 µm Hg to 5 µm Hg.

6. The method of claim 1, wherein the purification distillation is carried out prior to the denaturing distillation.

7. The method of claim 1, further comprising subjecting the composition comprising squalene to saponification, either before distillation steps (a) and (b), between distillation steps, or after distillation steps (a) and (b).

8. The method of claim 7, wherein saponification comprises the addition of NaOH or KOH to the composition comprising squalene.

9. A method for the manufacture of a pharmaceutically acceptable composition comprising preparing squalene according to claim 1.

10. The method according to claim 1, further comprising preparing an emulsion with squalene that has been subjected to the purification and denaturing distillations.

11. The method according to claim 10, further comprising combining the emulsion with an antigen.

12. The method according to claim 10, further comprising packaging the emulsion into a kit and packaging an antigen component into the kit.

13. The method of claim 12, wherein the emulsion component and the antigen component of the kit are in separate vials.

14. The method of claim 13, wherein the vials are made from borosilicate glass.

15. The method of claim 11, wherein the antigen is an influenza virus antigen.

16. The method of claim 15, wherein the combination of the emulsion and the antigen forms a vaccine composition and wherein the vaccine composition includes about 15 µg, about 10 µg, about 7.5 µg, about 5 µg, about 3.8 µg, about 3.75 µg, about 1.9 µg, or about 1.5 µg of hemagglutinin per influenza virus strain.

17. The method of claim 16, wherein the combination of the emulsion and the antigen forms a vaccine composition and wherein the vaccine composition includes a thiomersal or 2-phenoxyethanol preservative.

18. A method for re-distillation of a composition comprising 99% squalene or more, said method comprising:
  (i) providing a squalene-containing composition comprising 99% squalene or more from an animal source, wherein said squalene-containing composition has been obtained by a process of purification distillation carried out at a temperature $T_1$; and
  (ii) subjecting the composition from (i) to a re-distillation, said re-distillation being a denaturing distillation carried out at a temperature $T_2$; wherein $T_2 \geq 200°$ C.

* * * * *